United States Patent [19]

Spatz

[11] Patent Number: 4,588,735

[45] Date of Patent: May 13, 1986

[54] FUNGICIDAL (TRIHALOPHENOXY OR TRIHALOPHENTHIO) ALKYLAMINOALKYL PYRIDINES AND PYRROLES

[75] Inventor: David M. Spatz, Fairfax, Calif.

[73] Assignee: Chevron Research Company, San Francisco, Calif.

[21] Appl. No.: 470,824

[22] Filed: Feb. 28, 1983

[51] Int. Cl.$^4$ .............. A01N 43/36; A01N 43/40; C07D 213/38; C07D 207/335
[52] U.S. Cl. .................... 514/357; 514/427; 546/334; 548/561
[58] Field of Search ............... 546/334; 424/263, 274; 548/561; 514/357, 427

[56] References Cited

U.S. PATENT DOCUMENTS 3,960,878  6/1978  Peterson et al. ............. 546/334
4,381,305  4/1983  Casagrande et al. .......... 424/263
4,459,300  7/1984  Watts ..................... 424/263

Primary Examiner—Henry R. Jiles
Assistant Examiner—Dale A. Bjorkman
Attorney, Agent, or Firm—S. R. LaPaglia; T. G. DeJonghe; S. L. Biggs

[57] ABSTRACT

Compounds of the Formula:

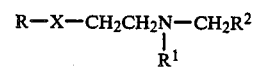

wherein
X is sulfur or oxygen;
R is phenyl or phenyl substituted with 1 to 3 substituents independently selected from fluoro, chloro, bromo, iodo, lower alkyl or trihalomethyl;
$R^1$ is lower alkyl or lower alkoxyalkyl; and
$R^2$ is 5- or 6-member heterocyclic ring having 1 to 3 ring nitrogens and the remainder of the ring atoms carbon atoms, optionally substituted with 1 to 2 independent lower alkyl groups, provided that a nitrogen of the 5- or 6-member heterocyclic ring is not bonded to the adjacent —CH$_2$— group; or the group —CH$_2$—R$^3$ wherein R$^3$ is a 5- or 6-member heterocyclic ring having 1 to 3 ring nitrogens and the remainder of the ring atoms carbon atoms, are fungicidal.

21 Claims, No Drawings

FUNGICIDAL (TRIHALOPHENOXY OR TRIHALOPHENTHIO) ALKYLAMINOALKYL PYRIDINES AND PYRROLES

BACKGROUND OF THE INVENTION

This invention is drawn to novel fungicides.

With the world more dependent for food on an ever decreasing amount of cultivated farmland, it is increasingly important to develop effective fungicides which protect crops from fungicidal destruction.

Kozlik et al., in CA 79:53327Z, disclosed 1-carbamoylimidazoles as insecticidal.

Brookes et al, in U.S. Pat. Nos. 4,080,462 and 3,991,071, disclosed 1-(N,N-disubstituted carbamoyl and thiocarbamoyl)-imidazoles as fungicidal.

Fungicidal components which are intermediates in the preparation of the compounds of this invention are disclosed in my copending and commonly-assigned U.S. patent applications "Substituted Heteroaryl Fungicides", Ser. No. 439,243, filed Nov. 4, 1982 and "Substituted Heteroaralkyl, Heteroaralkenyl or Halomethyl Fungicides", Ser. No. 443,009, filed Nov. 19, 1982.

SUMMARY OF THE INVENTION

The compounds of the present invention are represented by the formula:

$$R-X-CH_2CH_2-N(R^1)-CH_2R^2$$

wherein X is sulfur or oxygen; R is phenyl or phenyl substituted with 1 to 3 substituents independently selected from fluoro, chloro, bromo, iodo, lower alkyl or trihalomethyl; $R^1$ is lower alkyl or lower alkoxyalkyl; and $R^2$ is a 5- or 6-member heterocyclic ring having 1 to 3 ring nitrogens and the remainder of the ring atoms carbon atoms, optionally substituted with 1 to 2 independent lower alkyl groups, provided that a nitrogen of the 5- or 6-member heterocyclic ring is not bonded to the adjacent —CH$_2$— group, or the group —CH$_2$R$^3$ where $R^3$ is a 5- or 6-member heterocyclic ring having 1 to 3 ring nitrogens and the remainder of the ring atoms carbon atoms.

Among other factors, the present invention is based upon my finding that the compounds of this invention are effective fungicides. In particular, some of the compounds of this invention possess good activity against certain plant fungal diseases such as Bean Powdery Mildew and Tomato Early Blight.

In part due to their superior fungicidal activity, preferred R groups include the trihalophenyl group. Particularly preferred is the 2,4,6-trihalophenyl group.

Preferred halogens include bromo and chloro.

Preferred $R^1$ groups include n-propyl and ethoxyethyl. Particularly preferred is n-propyl.

Preferred $R^2$ groups include, for instance, 3-pyridyl, 5-pyrimidyl, 2-pyrazyl, 5-(1-methylimidazolyl), 1-methyl-1,2,4-triazolyl, 3-picolyl, 2-methyl-pyrazyl, and the like.

Definitions

As used herein, the following terms have the following means, unless expressly stated to the contrary.

The term "alkyl" refers to both straight- and branched-chain alkyl groups. Generally, such alkyl groups contain from 1 through 12 carbon atoms.

The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo or iodo.

The term "alkoxy" refers to the group R′O— wherein R′ is alkyl.

The term "lower alkoxy" refers to the alkoxy groups having from 1 through 6 carbon atoms and includes, for example, methoxy, ethoxy, t-butoxy, hexoxy, and the like.

The term "alkylene" refers to the group —(CH$_2$)$_z$—, where z is an integer greater than zero.

The term "lower alkylene" refers to alkylene groups having from 1 to 6 carbon atoms and includes, for example, methylene, ethylene, propylene, and the like.

The term "lower alkoxyalkyl" refers to groups having the formula-R″OR‴ wherein R″ is lower alkylene and R‴ is lower alkyl such that the total number of carbon atoms is not greater than 6. Typical lower alkoxyalkyl groups include, for instance, methoxymethyl, ethoxyethyl, methoxypropyl, isopropoxypropyl, ethoxybutyl, and the like.

The term "haloalkyl" refers to alkyl groups having one or more halo substituents. Typical haloalkyl groups include, for example, trifluoromethyl, dichloromethyl, bromochloromethyl, 1,2-dibromoethyl, 3-iodopropyl, chloromethyl, and the like.

The term "a 6-member heterocyclic ring containing 1 to 3 ring nitrogens" refers to groups such as pyridyl, pyridazinyl, pyrimidyl, pyrazyl, triazinyl, and the like.

The term "a 5-member heterocyclic ring containing 1 to 3 nitrogen atoms" refers to the groups such as imidazolyl, pyrrolyl, pyrazolyl, triazolyl, and the like.

The term "ethanolamine" refers to the group HOCH$_2$CH$_2$NH$_2$.

The term "N-(3-pyridylcarbonyl)ethanolamine" refers to the group:

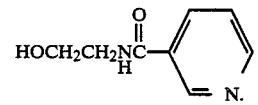

The term "N-(3-pyridylcarbonyl)ethanolamine 2,4,6-trichlorophenylether" refers to the group:

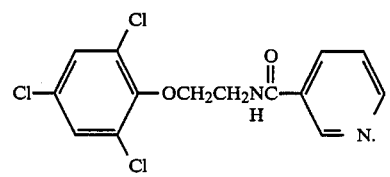

The term "N-(n-propyl), N-(3-pyridylcarbonyl)ethanolamine 2,4,6-trichlorophenylether" refers to the group:

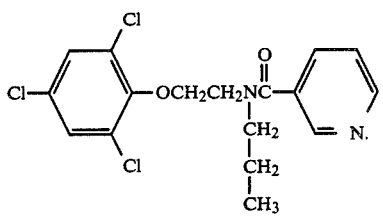

The term "2-aminoethanethiol" refers to the group HSCH₂CH₂NH₂.

The term "N-(3-pyridylcarbonyl), N-(n-propyl)2-aminoethanethiol" refers to the group:

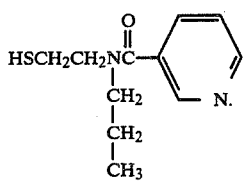

The term "N-(n-propyl), N-(3-pyridylcarbonyl)2-aminoethanethiol 4-t-butylphenylthioether" refers to the group:

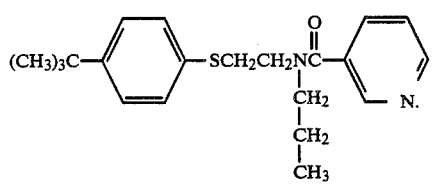

The term "a heterocycle containing a free nitrogen" refers to those heterocycles in which the nitrogen of the heterocycle is bonded with a hydrogen and includes, for instance, pyrrole (i.e.,

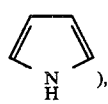

1,2,4-triazole (i.e.,

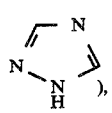

imidazole (i.e.,

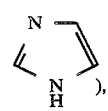

pyrazole (i.e.,

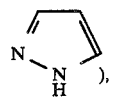

and the like.

The term "heteroaralkyl" refers to a lower alkyl group substituted with a 5- or 6-member heterocyclic ring containing 1 to 3 nitrogen atoms, and refers to the groups 1-methyl-1,2,4-triazolyl, 3-picolyl, and the like.

The term "ethylenediamine" refers to the group H₂NCH₂CH₂NH₂.

The term "nicotine amide" refers to the group:

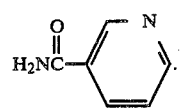

The term "pyrazinamide" refers to the group:

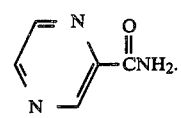

DETAILED DESCRIPTION OF THE INVENTION

The compounds of the present invention are conveniently prepared according to the following synthetic scheme:

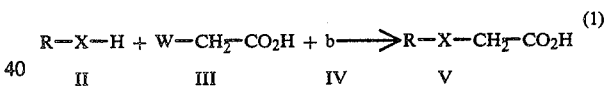

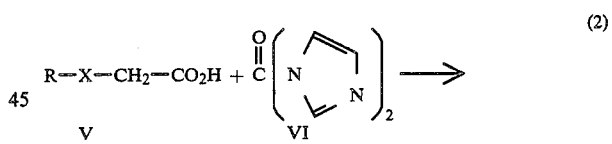

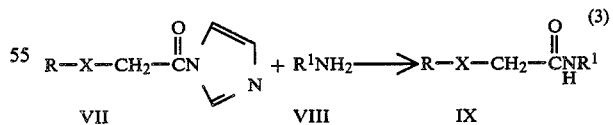

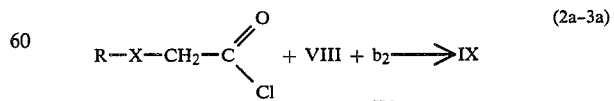

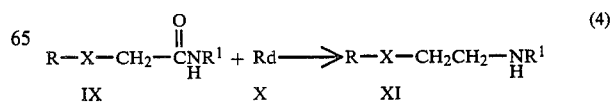

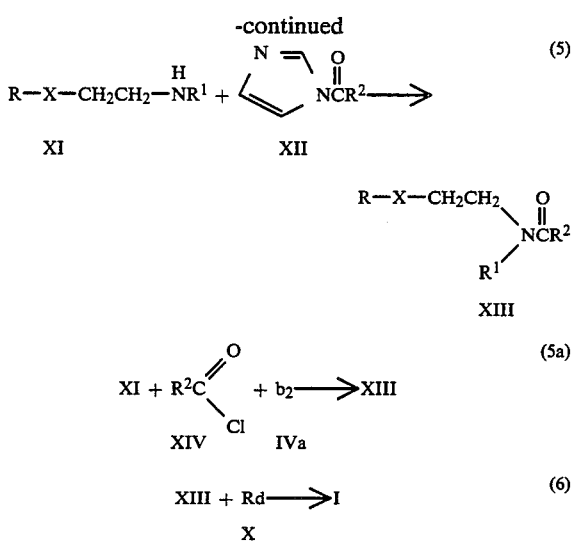

wherein R, $R^1$, $R^2$ and X are as defined above; W is a halogen, b is a base, $b_2$ is an acid scavenger (a base) and Rd is a reducing agent.

Reaction (1) is conducted by adding approximately 2 equivalents of a base, IV, to II. The reaction is done in the liquid phase employing an organic solvent such as ethanol, methanol, and the like, or, alternatively, water. Preferably, the base employed is an inorganic base. Suitable inorganic bases include, for instance, sodium hydride, sodium methoxide, metallic sodium, and the like. After addition of IV, an approximately equimolar amount of III, is added to the system. Reaction pressure is not critical and for convenience, the reaction is generally conducted at atmospheric pressure. The reaction is generally conducted at from 0° C. to 100° C., although preferably at from 40° C. to 70° C., and is generally complete from within 1 to 48 hours. The resulting intermediate, V, is isolated by conventional procedures such as extraction, filtration, chromatography, distillation, or alternatively, used in Reaction (2) without purification and/or isolation.

Reaction (2) is conducted by adding an essentially equimolar amount of carbonyldiimidazole, VI, to V. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting carboxylic acid imidazolide, VII, may be isolated by conventional procedures such as extraction, filtration, chromatography, distillation, and the like. Alternatively and preferably, the resulting intermediate is not isolated from the reaction solution but is used directly in Reaction (3).

Reaction (3) is conducted by adding an essentially equimolar amount of the appropriate primary amine, VIII, to VII. The reaction is conducted in the liquid phase using an inert anhydrous organic solvent such as chloroform, methylene chloride, dimethoxyethane, toluene, and the like. Preferably, the reaction solution is the same as was employed in Reaction (2) with the appropriate amine, VIII, merely added to the system after completion of Reaction (2). Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting amide, IX, is isolated by conventional procedures such as extraction, filtration, chromatography, distillation, or alternatively, used in Reaction (4) without purification and/or isolation.

Alternatively, IX may be prepared according to Reaction (2a–3a) by adding a solution of the acid chloride corresponding to V to a solution of VIII. The acid chloride Va is prepared from the acid V by techniques known to the art, such as treatment with thionyl chloride. The reaction is conducted in the presence of $b_2$ (IVa), an acid scavenger such as triethylamine, pyridine, an alkylamine, sodium carbonate, or the like. The reaction is conducted in the liquid phase using an inert organic solvent such as methylene chloride, chloroform, dioxane, toluene, and the like. The reaction is carried out at a temperature of about $-50°$ C. to about 100° C., preferably from about 0° C. to about 25° C. After the addition is complete, the reaction mixture is allowed to return to room temperature. The reaction is generally complete within about 0 to about 48 hours after the addition is complete. The resulting amide IX is isolated by conventional procedures such as extraction, filtration, chromatography, distillation, or alternatively used in Reaction (4) without further purification or isolation.

Reaction (4) is a conventional reduction of the amide to the amine. In preparing compounds of this invention, the carbonyl of the amide is reduced to the methylene group; the reaction is conveniently conducted by adding an essentially equimolar amount of a reducing agent, Rd, to IX. The reaction is conducted in the liquid phase employing an inert anhydrous organic solvent such as toluene, benzene, and the like. Suitable reducing agents include, for instance, lithium aluminum hydride, borane, borane methyl sulfide, and the like. Preferably, due to the ease in handling the reagent, borane methyl sulfide is employed as the reducing agent. Reaction pressure is not critical and for convenience, the reaction is conducted at atmospheric pressure. The reaction is generally conducted at from 0° C. to 110° C., although preferably at from 30° C. to 70° C., and is generally complete from within 1 to 24 hours. The resulting amine, XI, is isolated by conventional procedures such as extraction, filtration, chromatography, distillation, or alternatively, used in Reaction (5) without purification and/or isolation.

Reaction (5) is conducted by first preparing reagent XII. XII is prepared by adding an essentially equimolar amount of carbonyldiimidazole to the appropriate acid, $R^2CO_2H$ wherein $R^2$ is as defined above. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete within 1 to 24 hours. The resulting reagent, XII, may be isolated by conventional procedures such as extraction, filtration, chromatography, distillation, and the like. Alternatively and preferably, the reagent is not isolated from the reaction solution but an essentially equimolar amount of the amine, XI, is added to the system. Reaction pressure for this reaction is not critical and for convenience, the reaction is generally conducted at atmospheric pressure. After addition of XI, the reaction is generally conducted at room temperature and is generally complete from within 1 to 24 hours. The product, XIII, is then isolated by conventional procedures such as extraction, filtration, chromatography, and distillation, or alternatively, used in Reaction (6) without purification and/or isolation.

The preparation and fungicidal activity of amides of Formula XIII are disclosed in my copending and commonly-assigned U.S. patent applications "Substituted Heteroaryl Fungicides", Ser. No. 439,243, filed Nov. 4, 1982 and "Substituted Heteroaralkyl, Heteroaralkenyl or Halomethyl Fungicides", Ser. No. 443,009, filed Nov. 19, 1982.

Alternatively, XIII may be prepared by Reaction (5a) using the acid chloride XIV corresponding to $R^2CO_2H$. Acid chloride XIV may be conveniently prepared by combining approximately equimolar amounts of $R^2CO_2H$ and thionyl chloride. The reaction is conducted in the liquid phase using an inert organic solvent such as methylene chloride, toluene, chloroform, and the like. It is preferred to conduct the reaction in the presence of a catalytic amount of dimethylformamide. The reaction mixture is heated to reflux and refluxed for about 0 to about 24 hours. The mixture is stirred until gas evolution ceases. After the temperature of the mixture returns to room temperature, XIV may be used in Reaction (5a) without purification or isolation. Since XIV is susceptible to hydrolysis, minimal handling of it is preferred.

Reaction (5a) is conducted by combining XIV, with XI and IVa. The reaction is conducted in the liquid phase using an inert organic solvent such as methylene chloride, chloroform, toluene and the like. Suitable acid scavengers, $b_2$ (IVa), include bases such as triethylamine, pyridine, an alkylamine, sodium carbonate, and the like. The reaction is carried out at a temperature of about $-25°$ C. to about $100°$ C., preferably from about $0°$ C. to about $25°$ C., and may be conveniently carried out at room temperature. The reaction is generally complete within about 0 to about 24 hours. Product XIII is then isolated by conventional procedures such as extraction, filtration, chromatography, distillation, or alternatively, used in Reaction (6) without purification and/or isolation.

Reaction (6) is a conventional reduction of the amide to the amine. In preparing the compounds of this invention, the carbonyl of the amide XIII is reduced to a methylene group. The reaction is conveniently conducted by adding an essentially equimolar amount of a reducing agent, Rd, to XIII. The reaction is conducted in the liquid phase employing an inert anhydrous organic solvent such as toluene, benzene and the like. Preferably, due to the ease in handling the reagent, borane methyl sulfide is employed as the reducing agent. Reaction pressure is not critical and, for convenience, the reaction is conducted at atmospheric pressure. The reaction is generally conducted at from about $25°$ C. to about $110°$ C., although preferably at from about $50°$ C. to about $75°$ C. and is generally complete within from about 2 to about 18 hours. The resulting product, I, is isolated by conventional procedures such as extraction, filtration, chromatography, distillation or the like.

Alternatively, where $R^2$ is the group $-CH_2-R^3$ and where $R^3$ is a heterocycle containing a free nitrogen, the amides corresponding to the compounds of my invention are preferably prepared from the appropriate starting amine, XI, according to the following synthetic scheme:

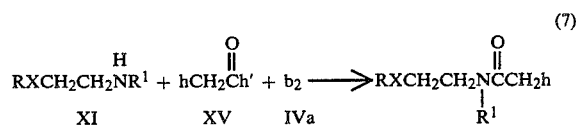

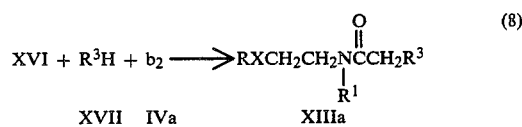

wherein $b_2$, X, R, $R^1$ and $R^3$ are as previously defined, and h and h' are independently halogen.

Reaction (7) is conducted by adding an essentially equimolar amount of an α-haloacetyl halide, XV, to XI. The reaction is conducted in the liquid phase employing an anhydrous aprotic organic solvent such as chloroform, methylene chloride, toluene, and the like. An essentially equimolar amount of a base, $b_2$, is added to the reaction to scavenge the acid generated. Preferably, $b_2$ is a base such as a trialkylamine (e.g., triethylamine), pyridine, sodium carbonate, or the like. Reaction pressure is not critical and for convenience, the reaction is generally conducted at atmospheric pressure. The reaction is generally conducted at from $0°$ C. to $100°$ C., although preferably at from $15°$ C. to $40°$ C., and is generally complete within 1 to 48 hours. The product XV is then isolated by conventional procedures such as extraction, filtration, chromatography, distillation, or alternatively used in Reaction (8) without purification and/or isolation.

Reaction (8) is conducted by adding an essentially equimolar amount of XVII to XVI. The reaction is conducted in the liquid phase employing an anhydrous aprotic organic solvent such as acetonitrile, toluene, dioxane, and the like. An essentially equimolar amount of a base, $b_2$, is optionally added to the reaction to scavenge the acid generated. Preferably, $b_2$ is a base such as pyridine, triethylamine, sodium carbonate, and the like. Reaction pressure is not critical and for convenience, the reaction is generally conducted at atmospheric pressure. The reaction is generally conducted at from $20°$ C. to $110°$ C., although preferably at $70°$ C. to $100°$ C., and is generally complete within 1 to 48 hours. The amide XIIIa is then isolated by conventional procedures such as extraction, filtration, chromatography, distillation, and the like, or alternatively reduced to the amine without purification and/or isolation.

The amide XIIIa is then converted to the compounds of this invention as outlined in Reaction (6).

Utility

The compounds of the invention are effective in controlling fungal infections. Some of the compounds of this invention are particularly effective in controlling powdery mildew fungal infections caused by the organism *Erysiphe polygoni*. Some of the compounds of this invention are also useful for controlling leaf blights caused by organisms such as *Phytophthora infestans conidia*, *Alternaria solani conidia*, and *Septoria apii*. Some of the compounds of this invention are also useful for controlling fungal infections caused by *Uromyces phaseoli tipica*, *Plasmopara viticola*, and *Piricularia oryzae*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

Compounds which were prepared in accordance with Examples 1 through 29 below are found in Table I.

EXAMPLES

Example 1

Preparation of 2,4,6-trichlorophenoxyacetic acid 2,4,6-trichlorophenol, 100.7 gm, was added to 250 ml of ethanol. 228.6 ml of a 25% solution of sodium methoxide (2 equivalents) in methanol were then added to the system. The system was stirred at room temperature for approximately 1 hour. Afterwards, 69.5 gm of bromoacetic acid was added and the system then heated to reflux. After 18 hours, an additional equivalent of sodium methoxide in methanol (114.3 ml) was added as well as 34.7 gm of bromoacetic acid. The system was continued at reflux for 12 hours. The reaction was then stopped and the solvent removed by stripping. The resulting solid was washed with water and then with ether. Concentrated HCl was next added to the solid and the system was left standing for 12 hours. Afterwards, the product was filtered, washed with water and air dried. Toluene was then added to the product. The toluene was removed by stripping and any remaining water was azeotroped off with the toluene. 74.4 gm of 2,4,6-trichlorophenoxyacetic acid was recovered.

Example 2

Preparation of N-(n-propyl)-2,4,6-trichlorophenoxyacetamide

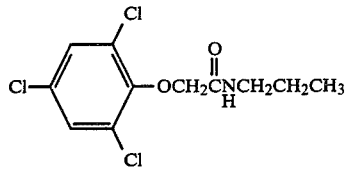

(a) 2,4,6-trichlorophenoxyacetic acid, 47.5 gm, was added to 300 ml of methylene chloride along with 30.3 gm of carbonyldiimidazole. The system was stirred overnight to give the carboxylic acid imidazolide.

(b) 15.4 ml of n-propylamine was then added to the system. The system was then stirred at room temperature for an additional 20 hours. The reaction was stopped and the organic solution was washed first with a dilute HCl solution, then with a sodium bicarbonate solution and then with water. The methylene chloride was removed by stripping to give the N-(n-propyl)-2,4,6-trichlorophenoxyacetamide.

Example 2a

Preparation of N-(n-propyl)-2,4,6-trichlorophenoxyacetamide

A solution of 2625 gm (9.62 moles) 2,4,6-trichlorophenoxyacetic acid chloride in methylene chloride (total solution weight 5403 gm) was added to a solution of 1251 gm (21.17 moles) n-propylamine in 7.6 l methylene chloride in a 22-liter flask over a period of 2 hours. During the addition, the temperature of the system was maintained at about 5° C. to 7° C. using a dry ice/isopropyl alcohol bath. During the addition, some white solids precipitated. After the addition was complete, the cooling bath was removed allowing the temperature of the system to rise to 10° C. over 25 minutes. The system temperature was then raised to 23° C. over 10 minutes by use of a warm water bath. Sample NMR and IR spectra indicate the reaction was complete. After removal of the warming bath, the methylene chloride solution was washed 3 times with 4 l water. The aqueous layer and organic layers were separated and the organic phase was dried over 150 gm magnesium sulfate. The organic solution was stripped until the weight reached about 3 kg. While the system was still in the hot water bath, 3.5 l hexane was added, giving a clear solution. The system was then cooled to 20° C., giving a very thick slurry of crystals. The crystals were filtered and washed with 2 l hexane. Air drying gave 2102 gm.

The mother liquor and hexane washings were stripped to give 450 gm of a brown oil which solidified upon cooling. Recrystallization from hexane (about 900 ml), followed by filtering the crystals, washing the crystals with hexane (about 500 ml), and air drying gave an additional 342 gm of the product.

Example 3

Preparation of N-(n-propyl)ethanolamine 2,4,6-trichlorophenylether

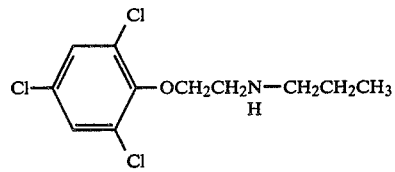

N-(n-propyl)-2,4,6-trichlorophenoxyacetamide, 44.0 gm, was added to 250 ml of toluene. 28 ml of borane methyl sulfide [BH$_3$.(CH$_3$)$_2$S] (2 equivalents) was then slowly added to the system. The system was heated at approximately 60° C. for 15 hours at which time reaction completion was checked by IR spectroscopy. 200 ml of methanol was then slowly added to the system. After addition of the methanol, the system was acidified by bubbling in HCl gas. Afterwards, the system was refluxed for 1 hour. The solvent was then removed by stripping. The resulting oil was dissolved in methanol which was then stripped. The oil was next dissolved in methylene chloride. The organic solution was washed with a sodium hydroxide solution and then with water. The methylene chloride was removed by stripping to give 36.3 gm of the N-(n-propyl)ethanolamine 2,4,6-trichlorophenylether, as a yellow oil.

Example 4

Preparation of N-(n-propyl), N-(2-pyrazinylcarbonyl)ethanolamine 2,4,6-trichlorophenylether

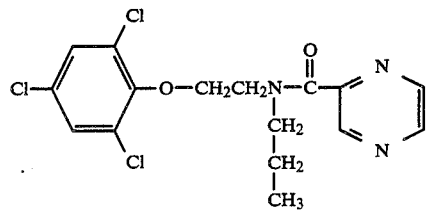

(a) 2-pyrazine carboxylic acid, 2.5 gm, was added to 10 ml of methylene chloride. 3.2 gm of carbonyldiimidazole was added to the system. The system was stirred at room temperature for 3 hours to give the 2-pyrazine carboxylic acid imidazolide.

(b) N-(n-propyl) ethanolamine 2,4,6-trichlorophenylether, 5.6 gm was then added to the system. The system was stirred at room temperature for 16 hours. The reaction was then stopped and the methylene chloride solution was washed with a sodium bicarbonate solution, then with a dilute solution of hydrochloric acid and finally with water. The methylene chloride solution was dried over magnesium sulfate and the methylene chloride removed by stripping to give 6.2 gm of the N-(n-propyl), N-(2-pyrazinylcarbonyl) ethanolamine 2,4,6-trichlorophenylether as a yellow oil.

Example 4a

Preparation of N-(n-propyl), N-(2-pyrazinylcarbonyl) ethanolamine 2,4,6-trichlorophenylether (a) 2-pyrazine carboxylic acid, 104.3 gm, and 105.9 gm thionyl chloride were added to 800 ml methylene chloride and 5 ml dimethylformamide. The system was heated to reflux, at which point gas evolution took place. The system was stirred at reflux until gas evolution ceased, after about 5 hours, to give the 2-pyrazine carboxylic acid chloride. The solution was cooled to room temperature and transferred to a dropping funnel for use in Step (b) without further isolation.

(b) To a solution of 214.9 gm of N-(n-propyl) ethanolamine 2,4,6-trichlorophenylether, the product of Example 3, and 84.84 gm triethylamine in 800 ml methylene chloride, the acid chloride of Step (a) was added dropwise at room temperature. After the addition was complete, the reaction mixture was stirred 10 minutes. The reaction mixture was then washed with water, then a 5% sodium bicarbonate solution, and then with water again. The mixture was dried over magnesium chloride and stripped to give 254 gm of an oil which solidified upon standing to give a solid with a melting point of 58°–61° C.

Example 5

Preparation of N-(n-propyl), N-(2-pyrazinylmethyl) ethanolamine 2,4,6-trichlorophenylether

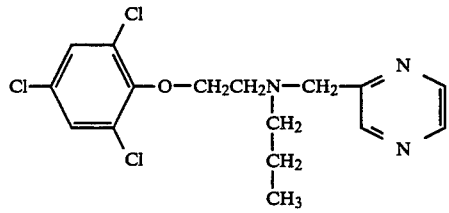

To a mixture of 5.8 g (0.015 moles) N-(n-propyl, N-(2-pyrazinylcarbonyl) ethanolamine 2,4,6-trichlorophenylether in 25 ml tetrahydrofuran, 1.4 ml (0.015 moles) borane-methyl sulfide are added slowly. The resulting mixture is refluxed overnight at low temperature (about 60° C.). The mixture is then cooled. Methanol (about 20 ml) is added slowly and the resulting mixture is acidified by bubbling in HCl gas. The acidified mixture is refluxed for about one hour and then is stripped. The residue is re-dissolved in about 20 ml methanol and the resulting mixture is stripped. The residue is then taken up in methylene chloride (about 100 ml) and the resulting solution is basified with a saturated aqueous sodium bicarbonate solution. The basified methylene chloride solution is washed with water and then filtered. The filtrate is stripped and the residue is dried with magnesium sulfate to give the product.

Example 6

Preparation of 2,6-dichlorothiophenoxyacetic acid 2,6-dichlorothiophenol, 50 gm, was added to 250 ml of ethanol. 63.8 ml of a 25% solution of sodium methoxide (2 equivalents) in methanol was then added to the system. The system was stirred at room temperature for approximately 3 hours. Afterwards, 20 ml of bromoacetic acid was added and the system then heated to reflux. The system was continued at reflux for 16 hours. The reaction was then stopped and the solvent removed by stripping. The resulting material was dissolved with basic aqueous solution and then washed with methylene chloride. Concentrated HCl was next added to the aqueous solution to acidify it. The product was extracted with methylene chloride. The methylene chloride solution was stripped and triturated with hexane.

The product was then filtered, washed with water and air dried to yield 55.3 gm of the title compound.

Example 7

Preparation of N-(n-propyl)-2,6-dichlorothiophenoxyacetamide (a) 2,6-dichlorothiophenoxyacetic acid, 55.3 gm, was added to 250 ml of methylene chloride along with 37.8 gm of carbonyldiimidazole. The system was stirred overnight at room temperature to give the carboxylic acid imidazolide.

(b) 19.1 ml of n-propylamine was then added to the system. The system was then stirred at room temperature for an additional 65 hours. The reaction was stopped and the organic solution was washed first with a dilute HCl solution, then with a sodium bicarbonate solution and then with water. The methylene chloride was removed by stripping to give 33.7 gm of the N-(n-propyl)-2,6-dichlorothiophenoxyacetamide.

Example 8

Preparation of N-(n-propyl) 2-aminoethanethiol 2,6-dichlorophenylthioether

N-(n-propyl)-2,6-dichlorothiophenoxyacetamide, 33.7 gm, was added to 250 ml of tetrahydrofuran. 34.4 ml of borane methyl sulfide (3 equivalents) was then slowly added to the system. The system was heated at approximately 55° C. for 18 hours at which time reaction completion was checked by IR spectroscopy. 200 ml of methanol was then slowly added to the system. After addition of the methanol, the system was acidified by bubbling in HCl gas. Afterwards, the system was refluxed for 1 hour. The solvent was then removed by stripping. The resulting oil was dissolved in methanol which was then stripped. The oil was next dissolved in methylene chloride. The organic solution was washed with a sodium hydroxide solution and then with water. The methylene chloride was removed by stripping to give 28.2 gm of the N-(n-propyl) 2-aminoethanethiol 2,6-dichlorophenylthioether.

Example 9

Preparation of N-(n-propyl), N-(3-pyridylcarbonyl) 2-aminoethanethiol 2,6-dichlorophenylthioether (a) 3-pyridine carboxylic acid, 2.5 gm, was added to 10 ml of methylene chloride. 3.2 gm of carbonyldiimidazole was added to the system. The system was stirred at room temperature for 16 hours to give the 3-pyridine carboxylic acid imidazolide.

(b) N-(n-propyl) 2-aminoethanethiol 2,6-dichlorophenylthioether, 5.3 gm, was then added to the system. The system was stirred at room temperature for 24 hours. The reaction was then stopped and the methylene chloride solution was washed with a sodium bicarbonate solution, and then with water. The methylene chloride solution was dried over magnesium sulfate and the methylene chloride removed by stripping to give 3.5 gm of the N-(n-propyl), N-(3-pyridylcarbonyl) 2-aminoethanethiol 2,6-dichlorophenylthioether as a yellow oil.

Example 10

Preparation of N-(n-propyl), N-(3-pyridylcarbonyl) ethanolamine 2,4,6-trichlorophenylether

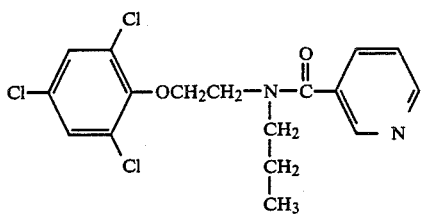

(a) 3-pyridine carboxylic acid, 3.1 gm, was added to 50 ml of methylene chloride. 4.0 gm of carbonyldiimidazole was added to the system. The system was stirred at room temperature for 2 hours to form the 3-pyridine carboxylic acid imidazolide.

(b) N-(n-propyl) ethanolamine 2,4,6-trichlorophenylether, 6.3 gm, was then added to the system. The system was stirred at room temperature for 18 hours. The reaction was then stopped and the methylene chloride was washed with a sodium bicarbonate solution and then with water. The methylene chloride solution was dried over magnesium sulfate and the methylene chloride removed by stripping to give 3.0 gm of the N-(n-propyl), N-(3-pyridinylcarbonyl) ethanolamine 2,4,6-trichlorophenylether. If desired, the crude compound may be further purified by recrystallization from hexane.

Example 10a

Preparation of N-(n-propyl), N-(3-pyridylcarbonyl) ethanolamine 2,4,6-trichlorophenylether (a) 3-pyridine carboxylic acid, 338 gm (2.75 moles) and 446 gm (2.75 moles) of carbonyldiimidazole were combined in 2.5 l methylene chloride. The system was heated gradually to reflux and stirred for a total of 1½ hours, at which time the system temperature was at methylene chloride reflux and carbon dioxide evolution had ceased, to give the 3-pyridine carboxylic acid imidazolide.

(b) To the above methylene chloride solution, 777 gm (2.75 moles) N-(n-propyl) ethanolamine 2,4,6-trichlorophenylether, the product of Example 3, was added and the system stirred at a gentle reflux over the weekend. The reaction was then stopped and the methylene chloride solution washed sequentially with water, then 5% HCl, then water, then 5% sodium bicarbonate solution, and then water again. The methylene chloride solution was dried over magnesium sulfate and stripped to give 775 gm of crude product, a yellow cake. The crude product was recrystallized from isopropyl alcohol (about 2 ml per gm crude product) to give a white solid with a melting point of 104°–106° C.

Elemental analysis for $C_{17}H_{17}N_2O_2Cl_3$ showed: calculated %C 52.6, %H 4.4, and %N 7.2; found %C 52.13, %H 4.65, and %N 7.16.

Example 11

Preparation of N-(n-propyl), N-(3-picolyl) ethanolamine 2,4,6-trichlorophenylether

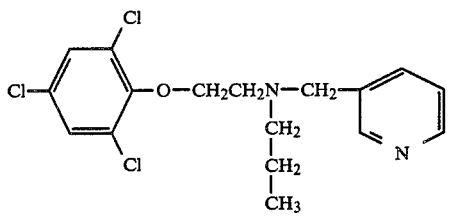

To a mixture of 5.8 gm (0.015 moles) N-(n-propyl), N-(3-pyridylcarbonyl) ethanolamine 2,4,6-trichlorophenylether in 25 ml tetrahydrofuran, 1.4 ml (0.015 moles) borane-methyl sulfide were added slowly. The resulting mixture was refluxed overnight at low temperature (about 60° C.). The mixture was then cooled. Methanol (about 20 ml) was added slowly and the resulting mixture acidified by bubbling in HCl gas. The acidified mixture was refluxed for one hour and then stripped. The residue was re-dissolved in about 20 ml methanol and the resulting mixture stripped. That residue was then taken up in methylene chloride (about 100 ml) and the resulting solution was basified with a saturated aqueous sodium bicarbonate solution. The basified methylene chloride mixture was washed with water and then filtered. Stripping of the filtrate, followed by drying over magnesium sulfate gave 4.2 gm of the product, a light yellow oil.

Elemental analysis for $C_{17}H_{19}N_2OCl_3$ showed: calculated %C 54.63; %H 5.12, and %N 7.49; found %C 53.19, %H 5.23, and %N 7.09.

Example 12

Preparation of N-(n-propyl), N-(5-pyrimidylcarbonyl) ethanolamine 2,4,6-trichlorophenylether

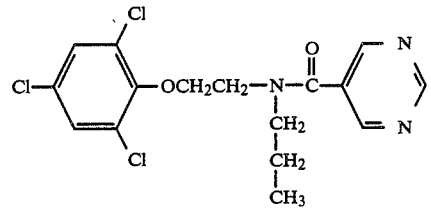

(a) 5-pyrimidyl carboxylic acid, 1.9 gm, was added to 30 ml of methylene chloride. 2.4 gm of carbonyldiimidazole was added to the system. The system was stirred at room temperature for 3 hours to form the 5-pyrimidyl carboxylic acid imidazolide.

(b) N-(n-propyl) ethanolamine 2,4,6-trichlorophenylether, 4.2 gm, was then added to the system. The system was stirred at room temperature for 18 hours. The reaction was then stopped and the methylene chloride was washed with a sodium bicarbonate solution, then with dilute HCl (pH about 3) and then with water. The methylene chloride solution was dried over magnesium sulfate and the methylene chloride removed by stripping to give 3.1 gm of the N-(n-propyl), N-(5-pyrimidylcarbonyl) ethanolamine 2,4,6-trichlorophenylether.

Example 13

Preparation of N-(n-propyl), N-(1-methyl-5-imidazolylcarbonyl) ethanolamine 2,4,6-trichlorophenylether

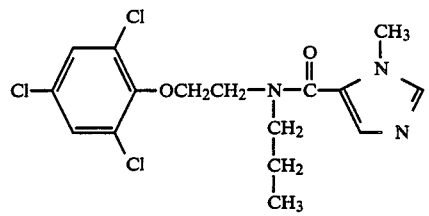

(a) 1-methyl-5-imidazole carboxylic acid, 7.0 gm, was added to 50 ml of methylene chloride. 5.2 gm of carbonyldiimidazole was added to the system. The system was stirred at room temperature for 18 hours to give the 1-methyl-5-imidazolyl carboxylic acid imidazolide.

(b) N-(n-propyl) ethanolamine 2,4,6-trichlorophenylether, 5.6 gm, was then added to the system. The system was stirred for room temperature for 24 hours. The reaction was then stopped and the methylene chloride was washed with a sodium bicarbonate solution and then with water. The methylene chloride solution was dried over magnesium sulfate and the methylene chloride removed by stripping to give 3.8 gm of the N-(n-propyl), N-(1-methyl-5-imidazolylcarbonyl) ethanolamine 2,4,6-trichlorophenylether.

Example 14

Preparation of N-ethoxyethyl-2,4,6-trichlorophenoxyacetamide

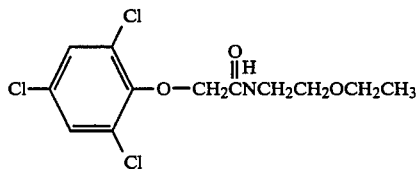

(a) To a stirred mixture of 37.3 g (0.146 moles) 2,4,6-trichlorophenoxyacetic acid in 300 ml methylene chloride, 23.7 g (0.146 moles) carbonyldiimidazole was added. The resulting mixture was stirred overnight to give the carboxylic acid imidazolide.

(b) To the imidazolide mixture of step (a), 13.0 g (0.146 moles) ethoxyethanolamine was added. The reaction mixture was then stirred overnight. The reaction was stopped and the methylene chloride solution was washed first with a saturated sodium bicarbonate solution and then with water. The methylene chloride mixture was filtered and the filtrate was stripped to remove the methylene chloride. The residue was dried over magnesium sulfate to give 34.0 g of the product, a light brown oil.

Elemental analysis for $C_{12}H_{14}NO_3Cl_3$ showed: calculated %C 44.04, %H 4.29, and %N 4.29; found %C 44.13, %H 4.53, and %N 4.52.

Example 15

Preparation of N-ethoxyethyl ethanolamine 2,4,6-trichlorophenylether hydrochloride

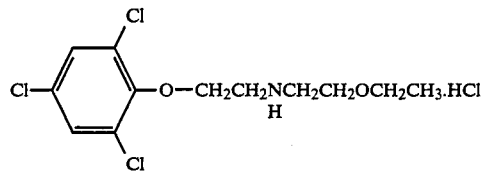

To a mixture of 31.5 g (0.096 moles) N-(ethoxyethyl)-2.4.6-trichlorophenoxyacetamide in about 200 ml toluene, 18.2 ml (2 equivalents) borane methyl sulfide were added slowly. The resulting mixture was heated to about 60° C. and maintained at that temperature overnight. After cooling, methanol (about 100 ml) was slowly added to the system. After the addition was complete, the mixture was acidified by bubbling in HCl gas. Afterwards, the system was refluxed for about an hour. The solvent was removed by stripping. The residue was re-dissolved in methanol (about 100 ml) and the resulting mixture stripped well. The residue was well dried in vacuum to give 34.6 g of the product, a white solid, melting point 85°–87° C.

Elemental analysis for $C_{12}H_{17}NO_2Cl_4$ showed: calculated %C 41.40, %H 4.63, and %N 4.02; found %C 41.25, %H 5.18, and %N 4.02.

Example 16

Preparation of N-ethoxyethyl, N-(3-pyridylcarbonyl) ethanolamine 2,4,6-trichlorophenylether

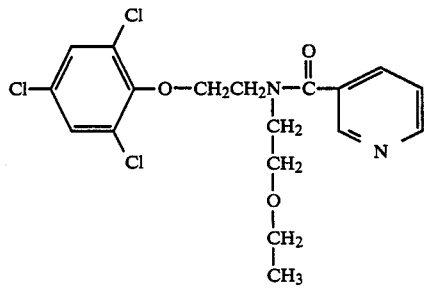

(a) A mixture of 7.4 g (0.06 moles) nicotinic acid and 9.7 (0.06 moles) carbonyldiimidazole in about 25 ml methylene chloride was stirred overnight to give the 3-pyridine carboxylic acid imidazolide.

(b) To the imidazolide mixture of step (a), 10.5 g (0.03 moles) N-(ethoxyethyl)ethanolamine 2,4,6-trichlorophenylether hydrochloride was added and the resulting mixture stirred at room temperature another day. The reaction was then stopped and the methylene chloride mixture was washed, first with a saturated aqueous sodium bicarbonate solution and then with water. The methylene chloride solution was filtered; the filtrate was stripped and the residue dried over magnesium sulfate. The residue was re-dissolved in methylene chloride (about 100 ml) and then washed with sodium carbonate in water with a little (about 0.5 g) tetrabutylammonium bromide. The methylene chloride mixture was then washed with water and filtered. The filtrate was stripped and the residue dried over magnesium sulfate to give 5.7 g of the product, a yellow oil.

Elemental analysis for $C_{18}H_{19}N_2O_3Cl_3$ showed: calculated %C 51.75, %H 4.58, and %N 6.71; found %C 52.7, %H 4.76, and %N 6.82.

Example 17

Preparation of N-ethoxyethyl, N-(3-picolyl) ethanolamine 2,4,6-trichlorophenylether

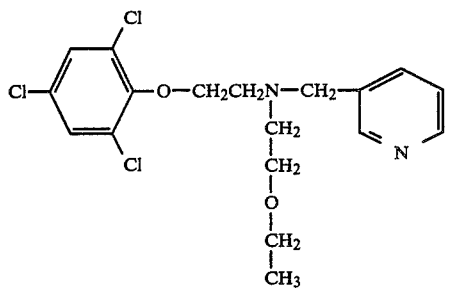

To a mixture of 3.2 (0.008 moles) of the product of Example 19 N-ethoxyethyl, N-(3-pyridylcarbonyl) ethanolamine 2,4,6-trichlorophenylether in about 25 ml toluene, 1.5 ml (0.016 moles) of borane-methyl sulfide were added slowly. After the addition was complete, the reaction mixture was heated to about 60° C. and maintained at that temperature over the weekend. The mixture was then cooled and about 20 ml methanol were added. The mixture was then acidified by bubbling in HCl gas and then refluxed for an hour. The solvent was stripped, the residue was re-dissolved in methanol, and the solvent was stripped again. The resulting residue was taken up in methylene chloride. The methylene chloride mixture was basified with dilute sodium hydroxide and washed well with water. Stripping of the solvent followed by drying with magnesium sulfate gave 2.1 gm of the product, a yellow oil.

Elemental analysis for $C_{18}H_{21}N_2O_2Cl_3$ showed: calculated %C 53.54, %H 5.24, and %N 6.94; found %C 50.76, %H 5.4, and %N 5.77.

Example 18

Preparation of N-(α-bromoacetyl), N-(n-propyl) ethanolamine 2,4,6-trichlorophenylether

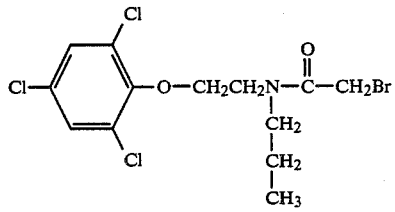

N-(n-propyl) ethanolamine 2,4,6-trichlorophenylether, 11.3 gm, was added to 100 ml of methylene chloride; 5.6 ml of triethylamine was added to the system. The system was stirred at about −70° C. for 5 minutes and then 3.5 ml of α-bromoacetyl bromide was added dropwise. The system was stirred at room temperature for an additional 18 hours. The reaction was stopped and the system poured into 100 ml of water. The product was extracted with methylene chloride. The organic solution was dried over magnesium sulfate and the methylene chloride was then removed by stripping to give the N-(α-bromoacetyl), N-(n-propyl) ethanolamine 2,4,6-trichlorophenylether as a brown oil.

Example 19

Preparation of N-[α-[1-(1,2,4-triazolyl)]acetyl], N-(n-propyl) ethanolamine 2,4,6-trichlorophenylether

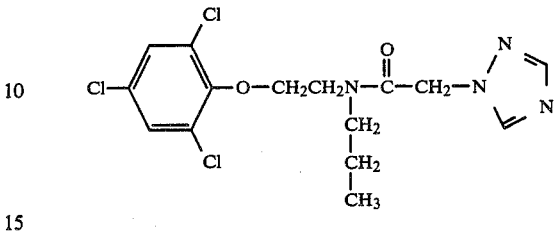

To a hot solution (about 60° C. to about 80° C.) of 3.6 gm potassium carbonate and 5.6 gm 1,2,4-triazole in 150 ml acetonitrile, 10.5 gm N-(α-bromoacetyl), N-(n-propyl) ethanolamine 2,4,6-trichlorophenylether, was added. The system was heated to reflux and maintained at reflux for 18 hours. The reaction mixture was then cooled and filtered; and the filtrate was stripped. The residue from the filtrate was dissolved in methylene chloride and washed twice with a saturated brine solution. The methylene chloride was stripped; the residue was then triturated with hexane to give the desired product.

Example 20

Preparation of N-[1-(1,2,4-triazolylethyl)], N-(n-propyl) ethanolamine 2,4,6-trichlorophenylether

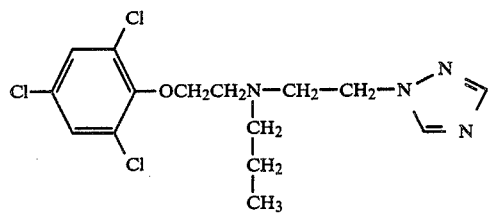

To a mixture of 4.1 gm (0.0105 moles) N-[α-[1-(1,2,4-triazolyl)]acetyl], N-(n-propyl) ethanolamine 2,4,6-trichlorophenylether in about 25 ml toluene, 2 ml (0.0210 moles) borane-methylsulfide were added slowly. The reaction mixture was heated to about 60° C. and kept at that temperature overnight. After cooling, about 20 ml methanol were added to the reaction mixture which was then acidified by bubbling HCl gas. The resulting mixture was then refluxed for one hour. The solvent was stripped, the residue taken up in about 20 ml methanol, and the solvent was stripped again. The resulting residue was then taken up in about 100 ml methylene chloride. The methylene chloride mixture was basified with dilute sodium hydroxide, washed well with water, and then filtered. Stripping of the solvent, followed by drying with magnesium sulfate gave 2.6 gm of the product, a thick yellow oil.

Elemental analysis for $C_{15}H_{19}N_4OCl_3$ showed: calculated %C 45.99, %H 4.37, and %N 14.30; found %C 45.44, %H 4.36, and %N 12.35.

Example 21

Preparation of N-(n-propyl), N-[α-(3-pyridyl)acetyl]ethanolamine 2,4,6-trichlorophenylether

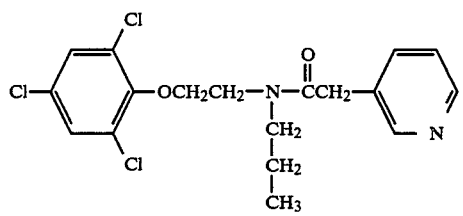

(a) α-(3-pyridyl)acetic acid, 6.8 gm, was added to 100 ml of methylene chloride. 8.1 gm of carbonyldiimidazole was added to the system. The system was stirred at room temperature for 5 hours to give the α-(3-pyridyl) acetic acid imidazolide.

(b) N-(n-propyl) ethanolamine 2,4,6-trichlorophenylether, the product of Example 3, 15.9 gm, was then added to the system. The system was stirred at room temperature for 16 hours. The reaction was then stopped and the methylene chloride solution was washed first with a sodium bicarbonate solution and then with water. The methylene chloride solution was dried over magnesium sulfate and the methylene chloride removed by stripping to give the desired product.

Example 22

Preparation of N-(n-propyl), N-(3-pyridylethyl) ethanolamine 2,4,6-trichlorophenylether

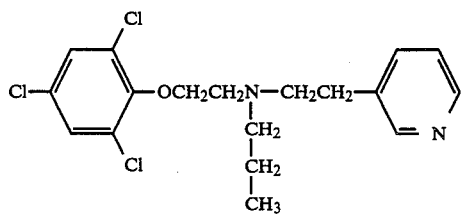

To a mixture of 6.0 g (0.015 moles) N-(n-propyl), N-[α-(3-pyridyl)acetyl]ethanolamine 2,4,6-trichlorophenylether in 25 ml tetrahydrofuran, 1.4 ml (0.015 moles) borane-methyl sulfide are added slowly. The resulting mixture is refluxed overnight at low temperature (about 60° C.). The mixture is then cooled. Methanol (about 20 ml) is added slowly and the resulting mixture is acidified by bubbling in HCl gas. The acidified mixture is refluxed for about one hour and is then stripped. The residue is re-dissolved in about 20 ml methanol and the resulting mixture is stripped. The residue is then taken up in about 20 ml methanol and the resulting mixture is then stripped. The residue is then taken up in methylene chloride (about 100 ml) and the resulting solution is basified with a saturated aqueous sodium bicarbonate solution. The basified methylene chloride solution is washed with water and then filtered. The filtrate is stripped and the residue is dried with magnesium sulfate to give the product.

Example 23

Preparation of N-(n-propyl), N-(α-chloroacetyl)2-aminoethanethiol 2,6-dichlorophenylthioether

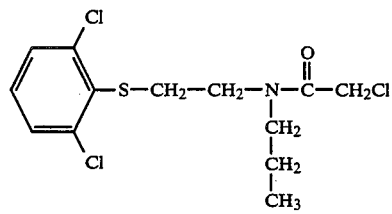

N-(n-propyl)2-aminoethanethiol 2,6-dichlorophenylthioether, 26.4 gm, is added to 100 ml of methylene chloride. 11 gm of triethylamine is added to the system. The system is stirred at room temperature for 5 minutes and then 11.3 gm of α-chloroacetyl chloride is added. The system is then stirred at room temperature for a 16 hours. The reaction is stopped and the system poured into 200 ml water. The product is extracted with methylene chloride. The methylene chloride solution is dried over magnesium sulfate and the methylene chloride is removed by stripping to give the desired product.

Example 24

Preparation of N-ethyl-2,4,6-trichlorophenoxyacetamide

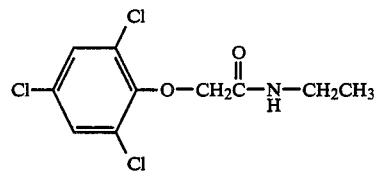

(a) 2,4,6-trichlorophenoxyacetic acid, the product of Example 1, 16.5 gm, was added to 150 ml of methylene chloride along with 10.5 gm of carbonyldiimidazole. The system was stirred overnight to give the 2,4,6-trichlorophenoxyacetic acid imidazolide.

(b) Excess ethylamine was bubbled into the imidazolide solution from Step (a). The system was then stirred at room temperature for an additional 24 hours. The reaction was stopped and the organic solution was washed first with a dilute HCl solution, then with a sodium bicarbonate solution, and then with water. The methylene chloride was removed by stripping to give the desired product.

Example 25

Preparation of N-ethyl ethanolamine 2,4,6-trichlorophenylether

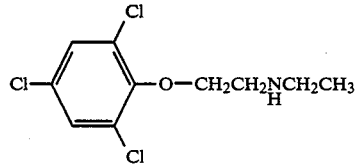

N-ethyl-2,4,6-trichlorophenoxyacetamide, the product of Example 13, 10.5 gm, was added to 80 ml of toluene. 7.0 ml of borane methyl sulfide [BH$_3$(CH$_3$)$_2$S]

(2 equivalents) was then slowly added to the system. The system was heated at approximately 60° C. for 18 hours at which time reaction completion was checked by IR spectroscopy. 50 ml of methanol was then slowly added to the system. After addition of the methanol, the system was acidified by bubbling in HCl gas. Afterwards, the system was refluxed for 1 hour. The solvent was removed by stripping. The resulting oil was dissolved in methanol which was then stripped. The oil was next dissolved in methylene chloride and the methylene chloride solution was washed with a sodium hydroxide solution and then with water. The methylene chloride was removed by stripping to give 10.0 gm of the N-ethyl ethanolamine 2,4,6-trichlorophenylether.

By reacting with the appropriate reagents, the following compounds are prepared from the N-ethyl ethanolamine 2,4,6-trichlorophenylether:

N-(α-bromoacetyl), N-ethyl ethanolamine 2,4,6-trichlorophenylether;

N-(α-chloroacetyl), N-ethyl ethanolamine 2,4,6-trichlorophenylether; and

N-[α-(3-pyridyl)acetyl], N-ethyl ethanolamine 2,4,6-trichlorophenylether.

Example 26

Preparation of 4-t-butylphenoxyacetic acid

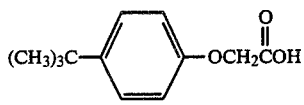

4-t-butylphenol, 37.5 gm, was added to 300 ml of ethanol. 57.2 gm of a 25% solution of sodium methoxide (2equivalents) in methanol was then added to the system. The system was stirred at room temperature for approximately 0.5 hour. Afterwards, 29.5 ml of bromoacetic acid was added and the system was then heated to reflux for 18 hours. The reaction was then stopped and the solvent removed by stripping. The resulting solid was dissolved in methylene chloride; dilute sodium hydroxide was added to give a basic pH. The resulting precipitate was dissolved in hydrochloric acid and then extracted with methylene chloride. The methylene chloride was then stripped, and the resulting crude product air dried. Toluene was then added to the product. The toluene was removed by stripping and any remaining water was azeotroped off with the toluene to give 33.3 gm of 4-t-butylphenoxyacetic acid.

Example 27

Preparation of N-(n-propyl)-4-t-butylphenoxyacetamide

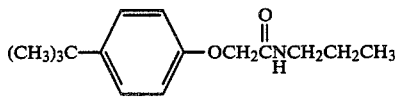

(a) 4-t-butylphenoxyacetic acid, the product of Example 15, 33.3 gm, was added to 300 ml of methlene chloride along with 26.4 gm of carbonyldiimidazole. The system was stirred overnight to give the 4-t-butylphenoxyacetic acid imidazolide.

(b) 13.4 ml of n-propylamine was then added to the system. The system was then stirred at room temperature for an additional 24 hours. The reaction was stopped and the organic solution was washed first with a dilute HCl solution, then with a sodium bicarbonate solution, and then with water. The methylene chloride was removed by stripping to give the N-(n-propyl)-4-t-butylphenoxyacetamide.

Example 28

Preparation of N-(n-propyl) ethanolamine 4-t-butylphenylether

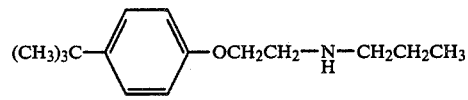

To 250 ml of a 1:1 mixture of toluene:tetrahydrofuran, 35.0 gm N-(n-propyl)-4-t-butylphenoxyacetamide, the product of Example 16, was added. The resulting mixture was heated to reflux and then 42.8 ml borane methylsulfide was added slowly. The reaction mixture was maintained at reflux for 48 hours at which time completion of the reaction was checked by IR spectroscopy. The reaction mixture was then cooled and 200 ml methanol was added slowly to the system. The system was then acidified by bubbling hydrogen chloride gas through it, and then heated to reflux and refluxed for 1 hour. The solvent was removed by stripping; the resulting oil was redissolved in methanol and the methanol stripped. The residue was dissolved in methylene chloride and basified with sodium hydroxide. The methylene chloride solution was then washed with water. The methylene chloride was stripped to give 31.2 gm of the N-(n-propyl)ethanolamine 4-t-butylphenylether.

Example 29

Preparation of N-(n-propyl), N-(α-chloroacetyl)ethanolamine 4-t-butylphenylether

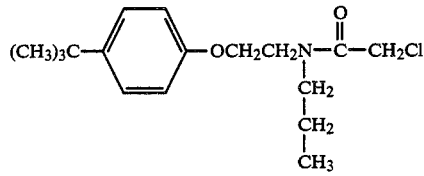

N-(n-propyl)ethanolamine 4-t-butylphenylether, 23.3 gm, is added to 100 ml of methylene chloride. 11 gm of triethylamine is added to the system. The system is stirred at room temperature for 5 minutes and then 11.3 gm of α-chloroacetyl chloride is added. The system is then stirred at room temperature for 16 hours. The reaction is stopped and the system was poured into 200 ml of water. The product is extracted with methylene chloride solution. The methylene chloride solution is dried over magnesium sulfate and the methylene chloride is removed by stripping to give the desired product.

Compounds made in accordance with Examples 1 to 29 are found in Table I.

By following the procedures of Examples 1 to 29 and using the appropriate starting materials and reagents, the following compounds are prepared:

N-(n-propyl), N-(5-pyrimidylmethyl)ethanolamine 2,4,6-trichlorophenylether;

N-(n-propyl), N-(5-(1-methyl-5-imidazolylmethyl))ethanolamine 2,4,6-trichlorophenylether;

N-(n-propyl), N-(3-picolyl) 2-aminoethanethiol 2,6-dichlorophenylthioether;
N-(n-propyl), N-[5(1-ethyl-imidazolylmethyl)]ethanolamine 2,4,6-trichlorophenylether;
N-(n-propyl), N-(5-pyrimidylmethyl)ethanolamine 4-t-butylphenylether;
N-methoxyethyl, N-(3-picolyl)ethanolamine 2,4,6-trichlorophenylether;
N-ethoxyethyl, N-(3-picolyl)ethanolamine 2,4,6-tribromophenylether;
N-ethoxyethyl, N-(3-picolyl)ethanolamine 2,4,6-triiodophenylether;
N-(n-propyl), N-(3-picolyl)ethanolamine 4-trifluoromethylphenylether;
N-(n-propyl), N-(3-picolyl)ethanolamine 2,6-dichlorophenylether;
N-(n-propyl), N-(2-pyrazinylmethyl)ethanolamine 4-t-butylphenylether;
N-(n-propyl), N-(3-picolyl)ethanolamine 4-t-butylphenylether;
N-(n-propyl), N-(2-pyrazinylmethyl)ethanolamine 2,4-dichlorophenylether;
N-(n-propyl), N-(3-picolyl)ethanolamine 2,4-dichlorophenylether;
N-(n-propyl), N-(2-picolyl)ethanolamine 2,4,6-trichlorophenylether;
N-(n-propyl), N-(4-picolyl)ethanolamine 2,4,6-trichlorophenylether;
N-(n-propyl), N-(3-picolyl)ethanolamine 2,4,6-trimethylphenylether;
N-(n-propyl), N-(2-pyrazinylmethyl)ethanolamine 2,4,6-trimethylphenylether;
N-(n-propyl), N-(5-pyrimidylmethyl)ethanolamine 2,4,6-trimethylphenylether;
N-ethoxyethyl, N-(2-pyrazinylmethyl)ethanolamine 2,4,6-trichlorophenylether;
N-ethyl, N-(3-picolyl)ethanolamine 2,4,6-trichlorophenylether;
N-ethyl, N-(2-pyrazinylmethyl)ethanolamine 2,4,6-trichlorophenylether;
N-(n-propyl), N-(2-pyrazinylmethyl) 2-aminoethanethiol 2,4,6-trichlorophenylthioether;
N-(n-propyl), N-(3-picolyl) 2-aminoethanethiol 2,4,6-trichlorophenylthioether;
N-(n-propyl), N-(5-pyrimidylmethyl) 2-aminoethanethiol 2,4,6-tribromophenylthioether;
N-(n-propyl), N-[5-(1-methyl-imidazolylmethyl)] 2-aminoethanethiol 2,4,6-trichlorophenylthioether;
N-(n-propyl), N-(5-pyrimidylmethyl) 2-aminoethanethiol 4-t-butylphenylthioether;
N-methoxyethyl, N-(3-picolyl) 2-aminoethanethiol 2,4,6-trichlorophenylthioether;
N-ethoxyethyl, N-[5-(1-methyl-imidazolylmethyl)] 2-aminoethanethiol 2,4,6-tribromophenylthioether;
N-ethoxyethyl, N-[5-(1-methyl-imidazolylmethyl)] 2-aminoethanethiol 2,4,6-triiodophenylthioether;
N-(n-propyl), N-(3-picolyl) 2-aminoethanethiol 4-trifluoromethylphenylthioether;
N-(n-propyl), N-(3-picolyl)ethanolamine 2,6-dichlorophenylether;
N-(n-propyl), N-(5-pyrimidylmethyl)ethanolamine 2,6-dichlorophenylether;
N-(n-propyl), N-(2-pyrazinylmethyl)ethanolamine 2,6-dichlorophenylether;
N-(n-butyl), N-(3-picolyl)ethanolamine 2,4,6-trichlorophenylether;
N-ethyl, N-(3-picolyl)ethanolamine phenylether;
N-ethyl, N-(2-pyrazinylmethyl) 2-aminoethanethiol 2,6-dichlorophenylthioether;
N-(n-propyl), N-(5-pyrimidylmethyl)ethanolamine 4-methylphenylether;
N-(n-butyl), N-(3-picolyl) 2-aminoethanethiol 4-ethylphenylthioether;
N-(n-propyl), N-(5-(1-methyl-imidazolylmethyl))ethanolamine phenylether;
N-methoxymethyl, N-[5-(1-methyl-imidazolylmethyl)] 2-aminoethanethiol phenylthioester;
N-(n-hexyl), N-(3-pyridylethyl)ethanolamine 2,6-dichlorophenylether;
N-(n-hexyl), N-(3-pyridylethyl) 2-aminoethanethiol 2,6-dichlorophenylthioether;
N-ethyl, N-(3-pyridylethyl)ethanolamine 2,6-dichlorophenylether;
N-ethyl, N-(3-pyridylethyl) 2-aminoethanethiol 2,6-dichlorophenylthioester;
N-(n-propyl), N-(5-pyrimidylethyl)ethanolamine 2,4,6-trichlorophenylthioether;
N-(n-propyl), N-(5-pyrimidylethyl) 2-aminoethanethiol 2,4,6-trichlorophenylthioether;
N-ethyl, N-(3-pyridylethyl)ethanolamine phenylether;
N-ethyl, N-(3-pyridylethyl) 2-aminoethanethiol phenylthioether;
N-(n-propyl), N-(5-pyrimidylethyl)ethanolamine 4-t-butylphenylether;
N-(n-propyl), N-(5-pyrimidylethyl) 2-aminoethanethiol 4-t-butylphenylthioether;
N-ethyl, N-(1-imidazolylethyl)ethanolamine 2,4,6-trichlorophenylether;
N-ethyl, N-(1-imidazolylethyl) 2-aminoethanethiol 2,4,6-trichlorophenylthioether;
N-ethyl, N-(3-pyrrolylethyl) 2-aminoethanethiol 2,4,6-tribromoophenylthioether;
N-ethyl, N-(3-pyrrolylethyl)ethanolamine 2,4,6-tribromophenylether;
N-(n-propyl), N-(2-pyrazinylethyl)ethanolamine 2,4,6-trichlorophenylether;
N-(n-propyl), N-(2-pyrazinylethyl) 2-aminoethanethiol 2,4,6-trichlorophenylthioether;
N-(n-propyl), N-[6-(1,2,4-triazinyl)-ethyl]ethanolamine 2,4,6-trichlorophenylether;
N-(n-propyl), N-[6-(1,2,4-triazinyl)-ethyl]2-aminoethanethiol 2,4,6-trichlorophenylthioether;
N-(n-propyl), N-[6-(1,2,4-triazinyl)-ethyl]ethanolamine 4-t-butylphenylether;
N-(n-propyl), N-[6-(1,2,4-triazinyl)-ethyl]2-aminoethanethiol 4-trifluoromethylphenylthioether;
N-(n-propyl), N-[1-(1,2,4-triazolyl)-ethyl]ethanolamine 4-t-butylphenylether;
N-(n-propyl), N-[1-(1,2,4-triazolyl)-ethyl]2-aminoethanethiol 2,6-dichlorophenylthioether;
N-(n-propyl), N-[1-(1,2,4-triazolyl)-ethyl]ethanolamine 2,6-dibromophenylether;
N-ethoxyethyl, N-[1-(1,2,4-triazolyl)-ethyl]ethanolamine 2,4-dichlorophenylether;
N-ethoxyethyl, N-(3-pyridylethyl)ethanolamine phenylether;
N-methoxyethyl], N-(2-pyrazinylethyl) 2-aminoethanethiol 2,4,6-trichlorophenylthioether; and
N-n-propoxyethyl, N-(3-pyridylethyl)ethanolamine 2,4,6-trichlorophenylether;

Example A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

Example B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

Example C

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

Example D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

Example E

Grape Downy Mildew

The compounds of this invention were tested for the control of the Grape Downy Mildew organism, *Plasmopara viticola*. Seedlings of *Vitis vinifera* var. Emperor (7+ weeks old) were used as hosts. The plants were sprayed with a 250 ppm solution of the test compound in an acetone and water solution containing a small amount of non-ionic emulsifier. The treated plants were inoculated one day later by spraying them with a spore suspension of the organism. The treated plants were then held in a greenhouse at a temperature of about 68° F. to about 72° F. (relative humidify varied between about 30 and about 99%) for 4 days. The plants were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table II.

Example F

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

Example G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

Example H and the data is taken after 24 hours. Fungicidal activities are measured by a zone of inhibited mycelial growth from the center of the paper strip in terms of mg/cm² needed for 99% control of the fungus ($ED_{99}$). The effectiveness of the compounds tested for fungicidal activity is reported in Table II in terms of the percent of the $ED_{99}$ of the test compound of the $ED_{99}$ of the standard Difolatan ®.

TABLE I

Compounds of the formula:

| Compound No. | $R^1$ | $R^2$ | Physical State | % Carbon Calc. | % Carbon Found | % Hydrogen Calc. | % Hydrogen Found | % Nitrogen Calc. | % Nitrogen Found |
|---|---|---|---|---|---|---|---|---|---|
| 1 38185 | —CH₂CH₂OCH₂CH₃ |  | yellow oil | 53.54 | 50.76 | 5.24 | 5.4 | 6.94 | 5.77 |
| 2 37141 | —CH₂CH₂CH₃ |  | light yellow oil | 54.63 | 53.19 | 5.12 | 5.23 | 7.49 | 7.09 |
| 3 38027 | —CH₂CH₂CH₃ | 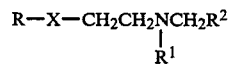 | yellow oil | 47.69 | 48.92 | 5.07 | 5.31 | 14.83 | 12.52 |

TABLE II

FUNGICIDAL ACTIVITY

| Compound No. | Phythium | Rhizoctonia | Fusarium | Botrytis | Asper. | GDM | TLB | CLB | TEB | BR | BPM | RB |
|---|---|---|---|---|---|---|---|---|---|---|---|---|
| 1 38185 | 0 | 0 | 0 | 0 | 0 | 0 | 0 | 7 | — | 0 | 59 | 40 |
| 2 37141 | 0 | 0 | 0 | 59 | 30 | 0 | 0 | 42 | 92 | 20 | 100 | 6 |
| 3 38027 | 0 | 0 | 0 | 13 | 64 | 10 | 0 | — | 64 | 0 | 25 | 8 |

GDM — Grape Downy Mildew (*Plasmopara viticola*)
TLB — Tomato Late Blight (*Phytophthora infestans*)
CLB — Celery Late Blight (*Septoria apii*)
TEB — Tomato Early Blight (*Alternaria solani* conidia)
BR — Bean Rust (*Uromyces phaseoli* tipica)
BPM — Bean Powdery Mildew (*Erysiphe polygoni*)
RB — Rice Blast (*Piricularia oryzae*)

Mycelial Inhibition

A number of the compounds of the present invention were evaluated for in vitro fungicidal effectiveness by means of a mycelial inhibition test. This test is designed to measure the fungitoxic activity of fungicidal chemicals in terms of their degree of inhibition of mycelium growth. Fungi used were *Phythium ultimum, Rhizoctonia solani, Fusarium monilofroma, Botrytis cinerea* and *Aspargillos niger*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C.

What is claimed is:

1. A compound of the formula:

$$R\text{—}X\text{—}CH_2CH_2NCH_2R^2$$
$$\overset{|}{R^1}$$

wherein X is sulfur or oxygen; R is trihalophenyl; $R^1$ is lower alkyl or lower alkoxyalkyl; and $R^2$ is an 5- or 6-membered aromatic heterocyclic ring having 1 ring nitrogen and the remainder of the ring atoms carbon atoms, optionally substituted with 1 to 2 independent lower alkyl groups or the group —CH₂R³ where R³ is a 5- or 6-membered aromatic heterocyclic ring having 1 ring nitrogen and the remainder of the ring atoms carbon atoms, provided that the ring nitrogen of $R^2$ or $R^3$ is not bonded to the adjacent —$CH_2$— group.

2. A compound of the formula defined in claim 1 wherein R is 2,4,6-trihalophenyl.

3. A compound of the formula defined in claim 2 wherein X is oxygen.

4. A compound of the formula defined in claim 3 wherein $R^2$ is 3-pyridyl or 3-picolyl.

5. A compound of the formula:

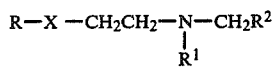

wherein X is sulfur or oxygen; R is 2,4,6-trichlorophenyl; $R^1$ is ethoxyethyl; and $R^2$ is 3-pyridyl or 3-picolyl.

6. A compound of the formula defined in claim 5 wherein $R^2$ is 3-pyridyl.

7. A compound of the formula defined in claim 4 wherein $R^1$ is propyl.

8. A compound of the formula defined in claim 7 wherein R is 2,4,6-trichlorophenyl.

9. A compound of the formula defined in claim 8 wherein $R^2$ is 3-pyridyl.

10. A method of controlling fungi which comprises contacting said fungi or their growth environment with a fungicidally effective amount of a compound of claim 1.

11. A method of controlling fungi which comprises contacting said fungi or their growth environment with a fungicidally effective amount of a compound of claim 2.

12. A method of controlling fungi which comprises contacting said fungi or their growth environment with a fungicidally effective amount of a compound of claim 4.

13. A method of controlling fungi which comprises contacting said fungi or their growth environment with a fungicidally effective amount of a compound of claim 6.

14. A method of controlling fungi which comprises contacting said fungi or their growth environment with a fungicidally effective amount of a compound of claim 8.

15. A method of controlling fungi which comprises contacting said fungi or their growth environment with a fungicidally effective amount of a compound of claim 9.

16. A fungicidal composition which comprises an inert carrier and a fungicidally effective amount of a compound of the formula:

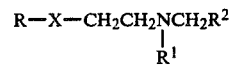

wherein X is sulfur or oxygen; R is trihalophenyl; $R^1$ is lower alkyl or lower alkoxyalkyl; and $R^2$ is an 5- or 6-membered aromatic heterocyclic ring having 1 ring nitrogen and the remainder of the ring atoms carbon atoms, optionally substituted with 1 to 2 independent lower alkyl groups or the group —$CH_2R^3$ where $R^3$ is a 5- or 6-membered aromatic heterocyclic ring having 1 ring nitrogen and the remainder of the ring atoms carbon atoms, provided that the ring nitrogen of $R^2$ or $R^3$ is not bonded to the adjacent —$CH_2$— group.

17. A fungicidal composition according to claim 16 which comprises an inert carrier and a fungicidally effective amount of a compound wherein $R^2$ is 3-pyridyl or 3-picolyl.

18. A fungicidal composition according to claim 16 which comprises an inert carrier and a fungicidally effective amount of a compound wherein X is oxygen, R is 2,4,6-trichlorophenyl, $R^1$ is ethoxyethyl, and $R^2$ is 3-pyridyl.

19. A fungicidal composition according to claim 17 which comprises an inert carrier and a fungicidally effective amount of a compound wherein X is oxygen, R is 2,4,6-trichlorophenyl and $R^1$ is propyl.

20. A fungicidal composition according to claim 19 which comprises an inert carrier and a fungicidally effective amount of a compound wherein $R^2$ is 3-pyridyl.

21. A fungicidal composition according to claim 16 which comprises an inert carrier and a fungicidally effective amount of a compound wherein R is 2,4,6-trihalophenyl.

* * * * *